US00PP23260P2

(12) United States Plant Patent
Fraser

(10) Patent No.: US PP23,260 P2
(45) Date of Patent: Dec. 18, 2012

(54) ***COPROSMA* PLANT NAMED 'INFERNO'**

(50) Latin Name: *Coprosma repens*
Varietal Denomination: Inferno

(76) Inventor: Peter Fraser, Waikato (NZ)

( * ) Notice: Subject to any disclaimer, the term of this patent is extended or adjusted under 35 U.S.C. 154(b) by 0 days.

(21) Appl. No.: 13/136,508

(22) Filed: Aug. 3, 2011

(51) Int. Cl.
*A01H 5/00* (2006.01)

(52) U.S. Cl. ..... Plt./226

(58) Field of Classification Search ..... Plt./226, Plt./263.1
See application file for complete search history.

(56) References Cited

OTHER PUBLICATIONS http://www.ballhort.com/Nursery/plant_info.aspx?phid=018701248002547 (*Coprosma* 'Inferno').*
PLUTO: Plant Variety Database (citation for *Coprosma* 'Inferno').*

* cited by examiner

*Primary Examiner* — Howard Locker
(74) *Attorney, Agent, or Firm* — Mark P. Bourgeois

(57) ABSTRACT

A new cultivar of *Coprosma* plant named 'Inferno' that is characterized by an upright habit and leaves that are green with orange margins in the summer and leaves that are dark purple with red margins in the winter.

1 Drawing Sheet

Botanical classification: *Coprosma repens.*
Variety denomination: 'Inferno'.

BACKGROUND OF THE INVENTION

The present invention relates to a new and distinct cultivar of *Coprosma* plant botanically known as *Coprosma repens* and hereinafter referred to by the cultivar name 'Inferno'.

The new cultivar was discovered by the inventor in a cultivated area of Kihikihi, Waikato, New Zealand in 2006. 'Inferno' was discovered as a naturally occurring branch mutation of *Coprosma* 'Evening Glow' (not patented).

Asexual reproduction by tip cuttings of the new cultivar 'Inferno' was first performed in 2006 in Kihikihi, Waikato, New Zealand. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Coprosma* cultivar 'Inferno'.

1. *Coprosma* 'Inferno' exhibits an upright habit.
2. *Coprosma* 'Inferno' exhibits leaves that are green with orange margins in the summer and leaves that are dark purple with red margins in the winter.

The closest comparison cultivar is the parent plant *Coprosma* 'Evening Glow'. The new cultivar 'Inferno' is distinguishable from 'Evening Glow' by the following characteristics:

1. 'Inferno' has leaves that are green with orange margins in the summer and leaves that are dark purple with red margins in the winter. The leaves of 'Evening Glow' in the summer are green when young, then turn orange when mature.
2. 'Inferno' has a more upright habit. 'Evening Glow' has a more spreading habit.

BRIEF DESCRIPTION OF THE DRAWING

The accompanying photograph illustrates the distinguishing traits of *Coprosma* 'Inferno'. The plant in the photograph shows an overall view of a 12 month old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Coprosma* cultivar named 'Inferno'. Data was collected in Kihikihi, Waikato, New Zealand from 12 month old outdoor grown plants in 2.5 liter containers. The time of year was Winter in the Southern Hemisphere and the average temperature range was 5 to 15 degrees Centigrade during the day and 2 to 8 degrees Centigrade at night. No photoperiodic treatments or growth retardants were used. Color determinations are in accordance with The Royal Horticultural Society Colour Chart 2001 edition, except where general color terms of ordinary dictionary significance are used. The growing requirements are similar to the species and include well drained soils and full to partial sun. 'Inferno' has not been tested under all possible conditions and phenotypic differences may be observed with variations in environmental, climatic, and cultural conditions, however, without any variance in genotype.

Botanical classification: *Coprosma repens* 'Inferno'.
Use: Ornamental perennial.
Parentage: 'Inferno' is a naturally occurring branch mutation of *Coprosma* 'Evening Glow'.
Vigor: Moderate.
Growth rate: Moderate.
Growth habit: Freely branching, dense, bushy habit.
Plant shape: Broad upright inverted triangle.
Suitable container size: 2.5 liter container.
Height: Average 1.5 m. in height.
Width: Average 1.5 m. in width.
Hardiness: Tolerant to −3 degrees Centigrade.
Propagation: Tip cuttings.
Time to initiate roots: Approximately 21 days in the Summer and 28 days in the Winter.

Time to produce a rooted cutting: Approximately 40 days in the Summer and 55 days in the Winter.

Root system: Fine and fibrous.

Lateral branches:

*Quantity*.—Approximately 24.

*Length*.—Average 15 cm.

*Diameter*.—Average 3 mm.

*Internode length*.—10 mm.

*Color*.—148B.

*Strength*.—Strong. Pinching is not required to encourage the development of branching.

Foliage:

*Texture*.—Smooth, glossy.

*Leaf arrangement*.—Opposite.

*Leaf attachment*.—Sessile.

*Compound or single*.—Single.

*Leaf shape*.—Obovate.

*Leaf apex*.—Obtuse.

*Leaf base*.—Rounded.

*Leaf length*.—Average 2.5 cm in length.

*Leaf width*.—1.2 cm in width.

*Pubescence*.—Absent.

*Leaf margin*.—Entire, unevenly recurved, slightly wavy.

*Vein pattern*.—Pinnate.

*Young leaf color* (*upper surface*).—N134B with margins 33B.

*Young leaf color* (*lower surface*).—N134B with margins 33B.

*Summer mature leaf color* (*upper surface*).—N134B with margins 33B.

*Summer mature leaf color* (*lower surface*).—N134B with margins 33B.

*Winter leaf color* (*both surfaces*).—187A with margins 44B.

*Durability of foliage to stress*.—Moderate to high.

Flowers: Flowers have not been observed.

Disease and insect resistance: Plants of the new *Coprosma* have not been observed for disease or insect resistance.

The invention claimed is:

1. A new and distinct variety of *Coprosma* plant named 'Inferno' as described and illustrated.

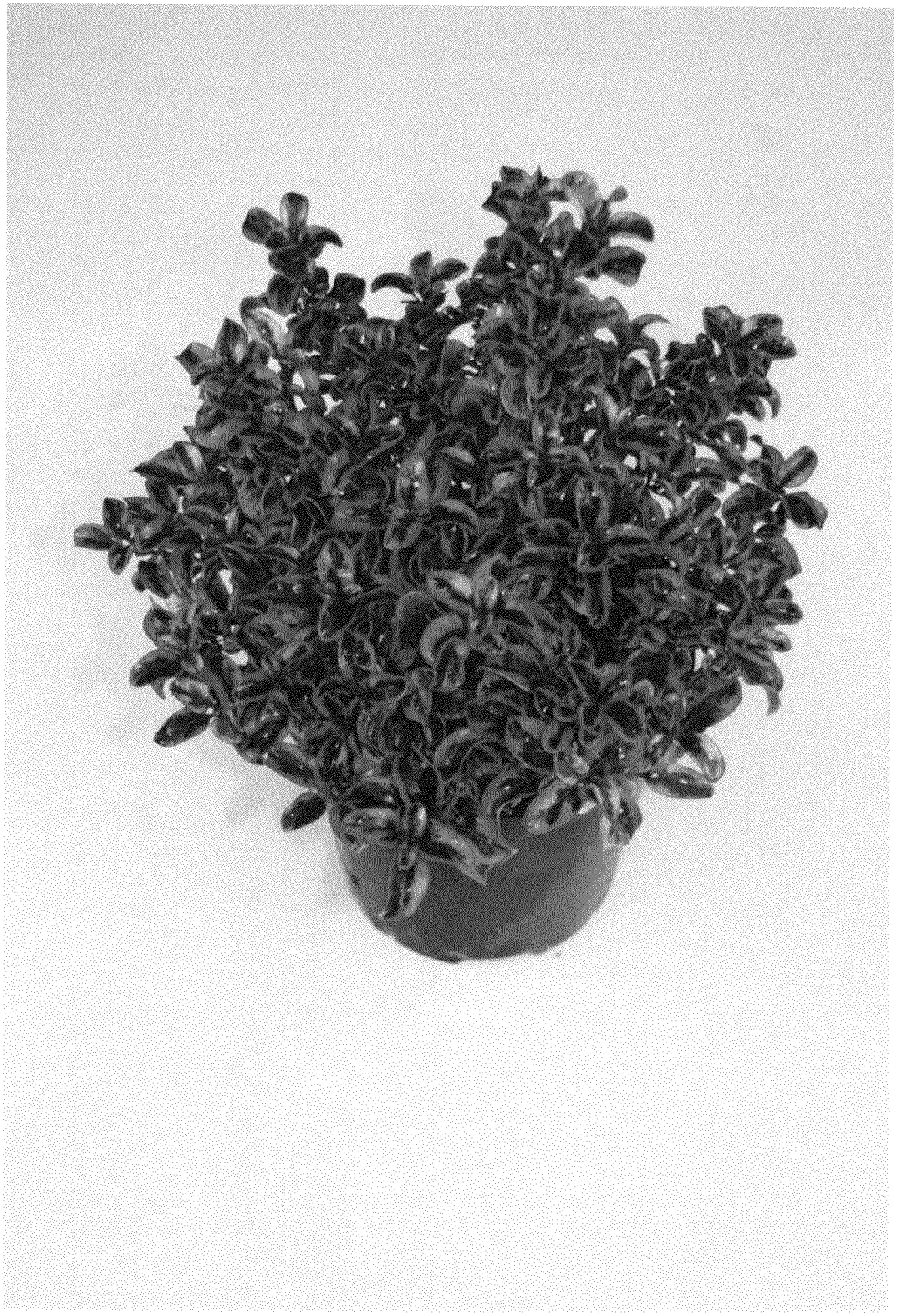

* * * * *